United States Patent
Miyazaki et al.

(10) Patent No.: US 8,246,321 B2
(45) Date of Patent: Aug. 21, 2012

(54) TUBE UNIT, CONTROL UNIT, AND MICROPUMP

(75) Inventors: Hajime Miyazaki, Matsumoto (JP); Mamoru Miyasaka, Shiojiri (JP); Kazuo Kawasumi, Chino (JP)

(73) Assignee: Seiko Epson Corporation (JP)

( * ) Notice: Subject to any disclaimer, the term of this patent is extended or adjusted under 35 U.S.C. 154(b) by 548 days.

(21) Appl. No.: 12/369,770

(22) Filed: Feb. 12, 2009

(65) Prior Publication Data

US 2009/0208350 A1    Aug. 20, 2009

(30) Foreign Application Priority Data

Feb. 14, 2008   (JP) .................................. 2008-032797
Oct. 30, 2008   (JP) .................................. 2008-279325

(51) Int. Cl.
*F04B 9/00*   (2006.01)
(52) U.S. Cl. ...................................................... 417/316
(58) Field of Classification Search .......... 417/415–416, 417/316–317
See application file for complete search history.

(56) References Cited

U.S. PATENT DOCUMENTS

2006/0073048 A1 *   4/2006   Malackowski ................ 417/474
2007/0128060 A1 *   6/2007   Miyazaki et al. ............. 417/474

FOREIGN PATENT DOCUMENTS

JP          3177742        4/2001
JP      2005351131 A   * 12/2005

* cited by examiner

*Primary Examiner* — Anh Mai
*Assistant Examiner* — Hana Featherly
(74) *Attorney, Agent, or Firm* — Harness, Dickey & Pierce, P.L.C.

(57) ABSTRACT

A micropump includes: a tube unit including a tube which has elasticity, and one portion of which is disposed in an arc shape, a plurality of fingers, which are disposed radiating from a direction of a center of the arc shape of the tube, and a guide frame, which holds the tube and the plurality of fingers; and a control unit including a cam, which sequentially presses the plurality of fingers in a direction in which a liquid flows, a drive force transmission mechanism, which transmits a torque to the cam, and a control circuitry, which carries out a control of a motor which drives the drive force transmission mechanism, wherein the tube unit and the control unit are attached stacked one on the other, and are detachable.

12 Claims, 5 Drawing Sheets

TUBE UNIT, CONTROL UNIT, AND MICROPUMP

CROSS REFERENCE TO RELATED ART

The disclosure of Japanese Patent Applications No. 2008-032797 filed on Feb. 14, 2008 and No. 2008-279325 filed on Oct. 30, 2008 including specification, drawings and claims is incorporated herein by reference in its entirety.

BACKGROUND

1. Technical Field

The present invention relates to a tube unit, a control unit, and a micropump configured by the units being connected in such a way as to be attachable and detachable.

2. Related Art

To date, a small peristaltic pump apparatus has been known in which a pump module, which includes a tube and a rotor which presses the tube, and a motor module, which has a step motor and an output gear mechanism, are assembled stacked one on the other, a gear acting as a connecting element is provided on a rotary shaft of the rotor, and a pinion acting as a power takeoff mechanism is provided on the output gear mechanism, wherein, on the pump module and the motor module being connected stacked one on the other, the pinion and the gear are connected (in mesh), and a drive force of the step motor is transmitted to the rotor (for example, refer to Japanese Patent No. 3,177,742 (Page 3, FIGS. 1 and 3)).

This kind of small peristaltic pump apparatus according to Japanese Patent No. 3,177,742 is configured by the pump module and the motor module being connected. Then, the small peristaltic pump apparatus is primarily used to be mounted directly on a living body, and inject a liquid medicine into it, requiring a high reliability, a durability, and a discharge accuracy.

In a pump apparatus which presses a tube, in particular, it being difficult to use the tube for a long period due to its deterioration, it is desirable that the tube is easily replaceable, or made disposable. However, it being difficult for a user to mount a soft and thin tube alone on a pump main body, it is conceivable that it affects a discharge performance.

Also, generally, a diameter of the tube varies widely, and this variation causes a variation in a tube pressing magnitude, leading to an impossibility of obtaining the discharge accuracy, as well as an overload on a small motor acting as a drive source, meaning that it is also conceivable that it is impossible to obtain a desired drive performance and, at worst, it is impossible to drive the apparatus.

SUMMARY

An advantage of some aspects of the invention is to solve at least a part of the problems mentioned above and the invention can be realized as the following aspects or application examples.

Application Example 1: A micropump according to this application example includes: a tube unit including a tube which has elasticity, and one portion of which is disposed in an arc shape, a plurality of fingers, which are disposed radiating from a direction of a center of the arc shape of the tube, and a guide frame, which holds the tube and the plurality of fingers; and a control unit including a cam, which sequentially presses the plurality of fingers in a direction in which a liquid flows, a drive force transmission mechanism, which transmits a torque to the cam, and a control circuitry, which carries out a control of a motor which drives the drive force transmission mechanism. The tube unit and the control unit are attached stacked one on the other, and are detachable.

According to this application example, as the tube and the fingers are formed into one unit by the guide frame, it being possible to replace the tube as the tube unit, it is possible for a user to easily carry out a tube replacement. Moreover, as it is possible to adjust a tube pressing magnitude by adjusting a finger length for each tube unit with respect to a variation in diameter of the tube, there is an advantage of easily ensuring a discharge accuracy.

Also, as the tube pressing magnitude is stabilized, it also being possible to make a maximum load torque of the motor a largely constant range, as well as it being possible to eliminate an overload on the motor, and obtain a desired drive performance, it is possible to prevent a kind of drive failure due to the overload, enabling a realization of a highly reliable micropump.

Furthermore, in a case in which a liquid to be used is a liquid medicine or the like, and in the event that the tube unit and a reservoir (to be described hereafter in an embodiment) containing the liquid medicine are formed into one unit, as the tube unit and the reservoir can simultaneously be replaced when the liquid medicine inside the reservoir runs out, it is possible, by a tube unit including a tube which makes direct contact with the liquid medicine being prepared for each targeted liquid medicine, to prevent a use of an erroneous kind of liquid medicine.

Application Example 2: In the micropump according to the heretofore described application example, it is preferable that the control unit includes the motor.

According to this kind of configuration, the tube unit is a unit formed of the tube, the plurality of fingers, and the guide frame, and the control unit is a unit formed of the cam, the drive force transmission mechanism, the motor, and the control circuitry. Consequently, as the tube unit has a smaller number of components, and is lower in cost, than the control unit, in the event that the control unit is made reusable, and the tube unit is made disposable, it is possible to reduce a running cost.

Application Example 3: In the micropump according to the heretofore described application example, it is preferable that the tube unit includes the motor.

According to this kind of configuration, the tube unit is a unit formed of the tube, the plurality of fingers, and the guide frame, and the control unit is a unit formed of the cam, the drive force transmission mechanism, the motor, and the control circuitry. Consequently, as it is possible to replace the motor as the tube unit when wanting to replace the tube, it being possible to always stably maintain a drive performance of the motor, it is also possible to use without worry a small and inexpensive motor, a drive endurance time of which is relatively short.

Also, as it is not necessary to replace the motor alone, there is an advantage that it is possible for the user himself/herself to easily replace the motor as the tube unit.

Application Example 4: In the micropump according to the heretofore described application example, it is preferable that the cam includes an outer circumferential surface, which is approximately perpendicular to a rotation plane of the cam, and has concavities and convexities which cause the plurality of fingers to press or release the tube, and a slope or a curved surface, which is continuous with the outer circumferential surface from a surface facing the tube unit, and that, when the tube unit is attached to the control unit, cam abutment portions of the plurality of fingers are moved to a position, in which they abut against the outer circumferential surface, along the slope or curved surface.

When the tube unit stands alone, a position of the fingers in a forward-back direction not being fixed, it may happen that the cam abutment portions cross the cam. Therein, by providing a finger guide surface on the cam, as the cam abutment portions of the fingers slide along the finger guide surface, and move to a space between the cam and the tube when the tube unit is attached to the control unit, it is possible to house the fingers in a position in which the tube can be pressed by the cam, without carrying out a special operation. Also, it is possible to prevent the cam or the fingers from being destroyed when the tube unit is attached to the control unit.

Application Example 5: In the micropump according to the heretofore described application example, it is preferable that a positioning member is provided for approximately aligning a rotation center of the cam with a center of an arc of a tube guide wall in at least a range in which the plurality of fingers press the tube, when the tube unit is attached to the control unit.

In the micropump, as the plurality of fingers are moved in a direction in which to press the tube by the cam rotating, they are each disposed radiating from the rotation center of the cam. Consequently, as the center of the arc of the tube guide wall and the rotation center of the cam coincide by providing the positioning member, it being possible to make an amount of movement of each of the plurality of fingers constant, it is possible to suppress a variation in the amount of movement of each finger (that is, the tube pressing magnitude).

Application Example 6: In the micropump according to the heretofore described application example, it is preferable that the cam abutment portions of the plurality of fingers are formed as a smooth curved surface, or formed of a low friction coefficient material.

As heretofore described, when the tube unit is attached to the control unit, the cam abutment portions slide along the finger guide surface, and the fingers move to the space between the cam and the tube. Also, when driving the micropump, the outer circumferential surface of the cam slidingly presses the cam abutment portions. Consequently, a friction load occurring due to the sliding being reduced by preparing the cam abutment portions so as to have a low friction coefficient, it is possible to reduce a load on the motor, and improve a drive stability and endurance.

Application Example 7: In the micropump according to the heretofore described application example, it is preferable that an elastic member is provided between the tube guide wall, provided in the guide frame and subject to a pressure of the plurality of fingers, and the tube.

According to this kind of configuration, by an excess pressure being absorbed by the elastic member when the tube is pressed by the fingers, it is possible to improve a resistance of the tube to a structure in which the tube is pressed directly against the tube guide wall.

It is more effective to use a low friction coefficient material as the elastic member.

Application Example 8: In the micropump according to the heretofore described application example, it is preferable that, the control unit further including a cam holding member which pivotally supports the cam, a tilt suppressing protrusion which suppresses a tilt of the cam in a direction of thickness is provided on the cam or the cam holding member.

According to this kind of configuration, by providing the cam or the cam holding member with the tilt suppressing protrusion which suppresses the tilt of the cam in the direction of thickness, it is possible, when the tube unit is attached to the control unit, to prevent the cam abutment portions riding on the finger guide surface, and the cam being tilted to impede a movement of the fingers to an appropriate position.

Also, it is also possible, when driving the micropump, to prevent a condition in which the fingers press the tube varyingly due to a wobbly rotation of the cam in the direction of thickness.

Application Example 9: A tube unit according to this application example, which is attachable to and detachable from the control unit according to the heretofore described application example, includes a tube, which has elasticity, a plurality of fingers, which sequentially press the tube in a direction in which a liquid flows, and a guide frame, which holds them.

According to this application example, a configuration being such that the tube unit is attachable to and detachable from the control unit, in a case of causing the liquid medicine or the like to flow, it is possible to enhance a reliability by arranging in such a way that the tube unit including the tube, which makes direct contact with the liquid medicine and has a low resistance, is renewed after each use. Also, as a number of components is small, and a reduction in cost is possible, it is possible to reduce the running cost.

Application Example 10: It is preferable that the tube unit according to the heretofore described application example includes the tube, the plurality of fingers, a motor, which drives a drive force transmission mechanism which transmits a torque to a cam which sequentially presses the plurality of fingers in the direction in which the liquid flows, and a guide frame, which holds them.

According to this application example, the motor being included in the tube unit, as it is possible to easily replace the motor as the tube unit when wanting to replace the tube, it being possible to always stably maintain the drive performance of the motor, it is also possible to use without worry a small and inexpensive motor, a drive endurance time of which is relatively short.

Application Example 11: In the tube unit according to the heretofore described application example, it is preferable that each of the plurality of fingers includes a shaft, a cam abutment portion provided at one end of the shaft, and a tube pressing portion which, being provided at the other end, is configured of a flange like protrusion, and that a groove, which houses the tube pressing portion and has a finger position regulation wall which regulates a position of each of the plurality of fingers in a forward-back direction, is provided in the guide frame.

According to this kind of configuration, by regulating the position of the fingers by means of the flange like protrusions provided on the fingers, and the grooves provided in the tube frame, it is possible to prevent the fingers from coming off the guide frame when the tube unit stands alone.

Also, as the position of the fingers in the forward-back direction is also regulated when the tube unit is attached to the control unit, it is possible to abut the cam abutment portions of the fingers against the finger guide surface, and reliably move the fingers to a predetermined position. By this means, it is possible to prevent the cam or the fingers from being destroyed.

Application Example 12: In the tube unit according to the heretofore described application example, it is preferable that each of the plurality of fingers includes a shaft, a cam abutment portion provided at one end of the shaft, and a tube pressing portion provided at the other end, that a flange like protrusion is provided partway along the shaft, and that a groove, which houses the flange like protrusion and regulates a position of each of the plurality of fingers in a forward-back direction, is provided in the guide frame.

According to this kind of configuration, by regulating the position of the fingers by means of the flange like protrusions provided on the fingers, and the grooves provided in the tube frame, it is possible to prevent the fingers from coming off the guide frame when the tube unit stands alone.

Also, as the position of the fingers in the forward-back direction is also regulated when the tube unit is attached to the control unit, it is possible to abut the cam abutment portions of the fingers against the finger guide surface, and reliably move the fingers to the predetermined position. By this means, it is possible to prevent the cam or the fingers from being destroyed.

Application Example 13: In the tube unit according to the heretofore described application example, it is preferable that the plurality of fingers are held on the guide frame in a position in which they do not press the tube, or in a condition in which they press the tube to the extent that the tube does not deteriorate.

According to this kind of configuration, it is possible to prevent a deterioration of the tube caused in the event that the tube is maintained in a pressed condition over a long period.

Application Example 14: A control unit according to this application example, which is attachable to and detachable from the tube unit according to the heretofore described application example, includes a cam, which sequentially presses a plurality of fingers in a direction in which a liquid flows, a drive force transmission mechanism, which transmits a torque to the cam, and a control circuitry, which carries out a drive control of a motor which drives the drive force transmission mechanism.

According to this application example, as the control unit is not provided with a motor, which is inferior in endurance to the drive force transmission mechanism and the control circuitry, it is possible to continue to use the control unit over a longer period.

Application Example 15: It is preferable that the control unit according to the heretofore described application example includes the cam, the drive force transmission mechanism, the control circuitry, and the motor.

According to this kind of configuration, as the control unit includes the motor, it not being necessary to bring the motor and the drive force transmission mechanism out of engagement, it is possible to make a drive system formed of the motor and the drive force transmission mechanism a configuration having a stable engagement condition.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereafter, a description will be given of embodiments of the invention, based on the drawings.

Figure 3:
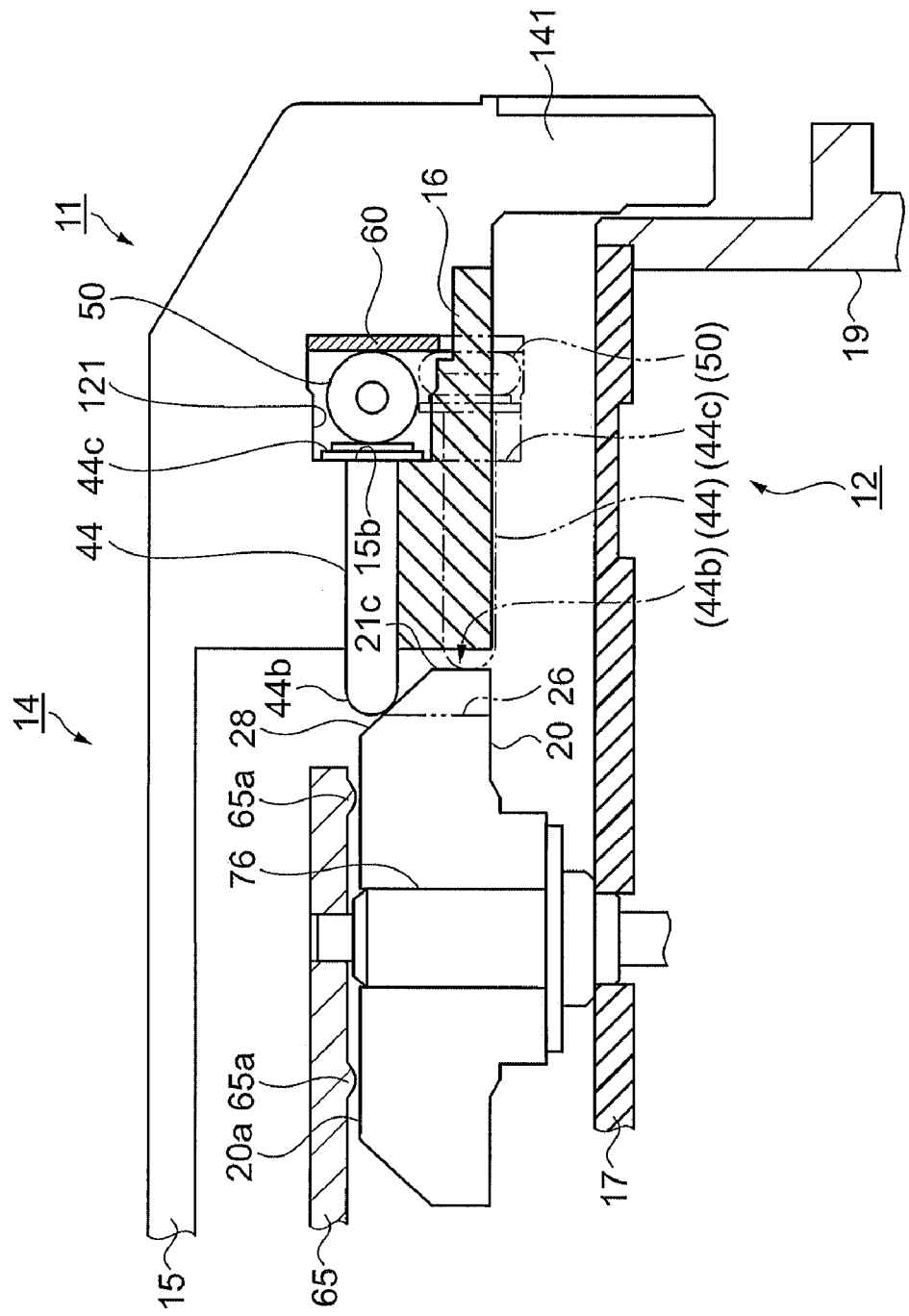
FIG. 3 is a fragmentary sectional view showing a structure of engagement between a plurality of fingers and a cam in the embodiment 1.
Figure 4:
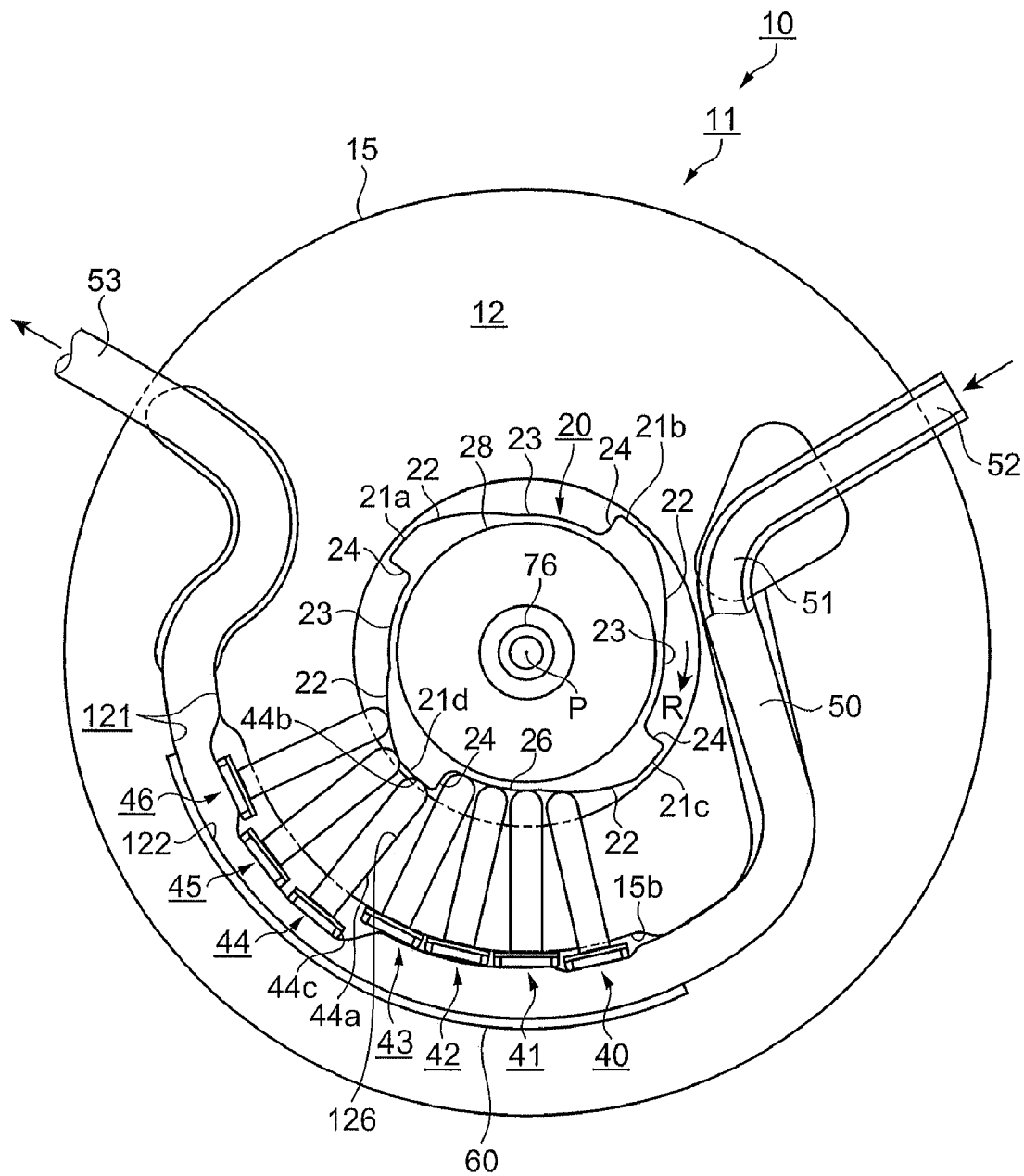
FIG. 4 is a plan view showing an outline structure of a tube unit according to the embodiment 1.
Figure 5:
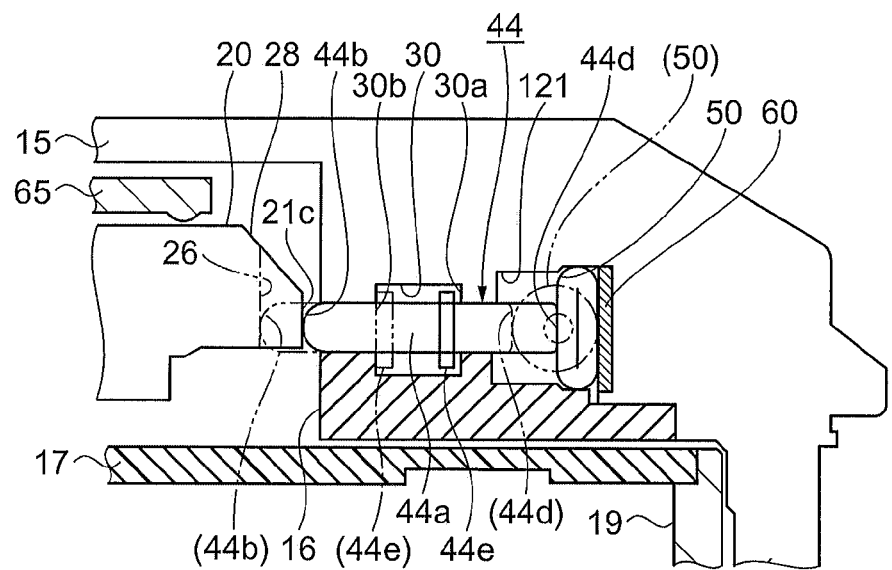
FIG. 5 is a fragmentary sectional view showing a micropump according to another example of the embodiment 1.
Figure 6:
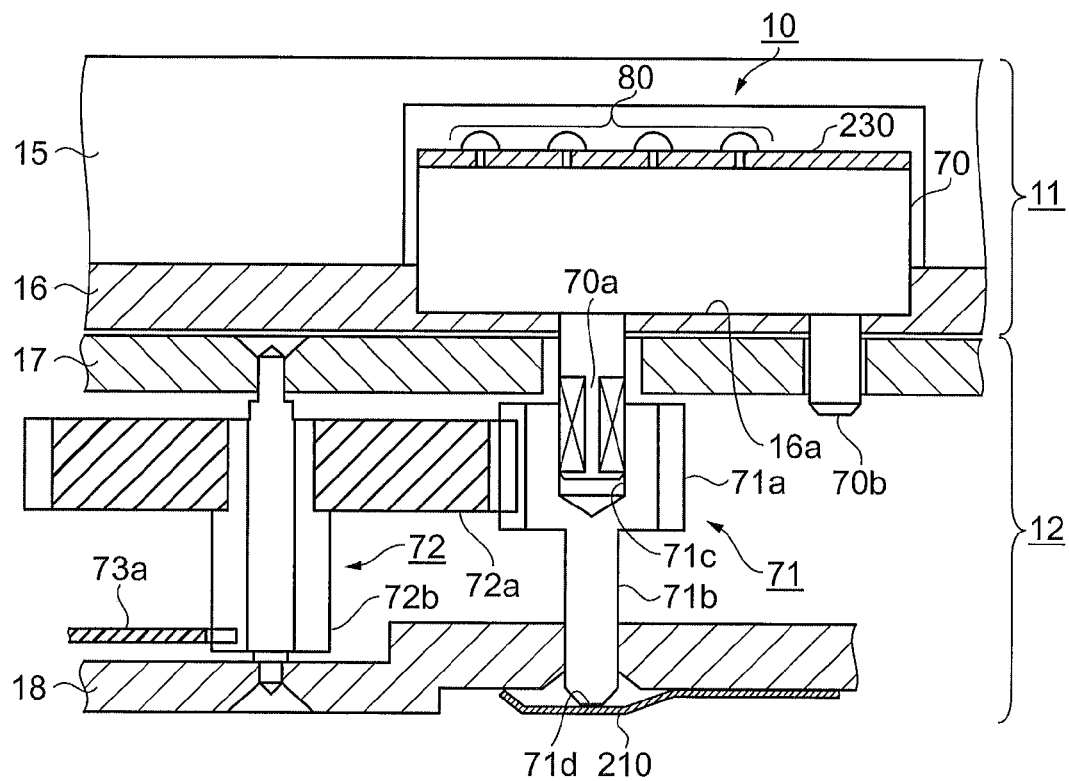
FIG. 6 is a fragmentary sectional view showing a micropump according to an embodiment 2.

FIGS. 1 to 4 show a micropump according to an embodiment 1, FIG. 5 shows a micropump according to another example of the embodiment 1, and FIG. 6 shows a micropump according to an embodiment 2.

The drawings referred to in the following descriptions are schematic views in which a vertical and horizontal scale of members and parts is different from an actual one.

Embodiment 1

Figure 1:
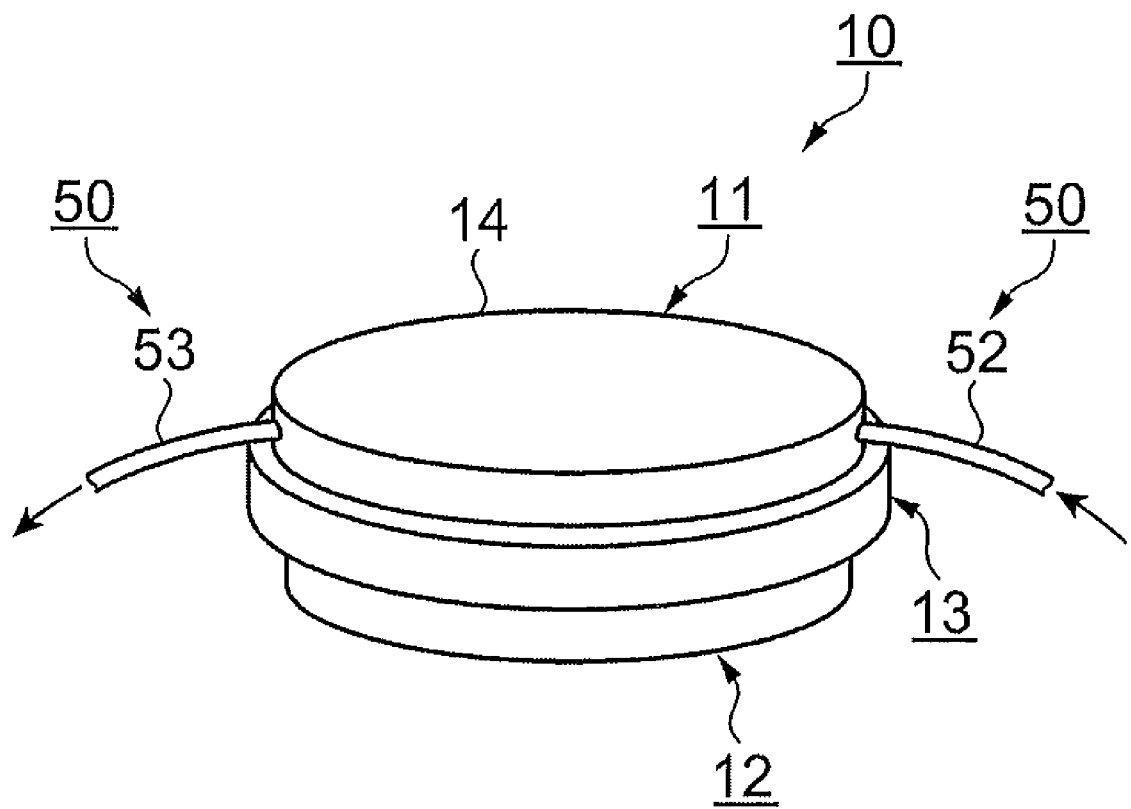
FIG. 1 is a perspective view showing an outline configuration of one aspect of a micropump according to an embodiment 1.

FIG. 1 is a perspective view showing an outline configuration of one aspect of the micropump according to the embodiment 1. In FIG. 1, the micropump 10 is configured of a tube unit 11, a control unit 12, and a connecting member 13 which connects the tube unit 11 and the control unit 12. The tube unit 11 is configured of a tube 50 having elasticity, a plurality of fingers (not shown), which press the tube 50, and a guide frame 14, which holds the tube 50 and the plurality of fingers. Also, the control unit 12 is configured of a motor acting as a drive source, a drive force transmission mechanism, which transmits a drive force to a cam shaft, and a control circuitry, which performs a drive control of the motor (none of which are shown).

The tube 50 mounted in the tube unit 11 has a flow inlet portion 52, which causes a liquid to flow in from a reservoir (not shown) containing the liquid, and a flow outlet portion 53, which discharges the liquid, protruded from the tube unit 11. It is also acceptable to adopt a structure in which the reservoir is provided inside the tube unit 11, and connected to the flow inlet portion 52 inside the tube unit 11. The tube unit 11 and the control unit 12 are stacked one on the other, and closely fixed by the connecting member 13. Consequently, an interior of the micropump 10 other than the flow inlet portion 52 and flow outlet portion 53 of the tube 50 is of a waterproof structure.

Figure 2:
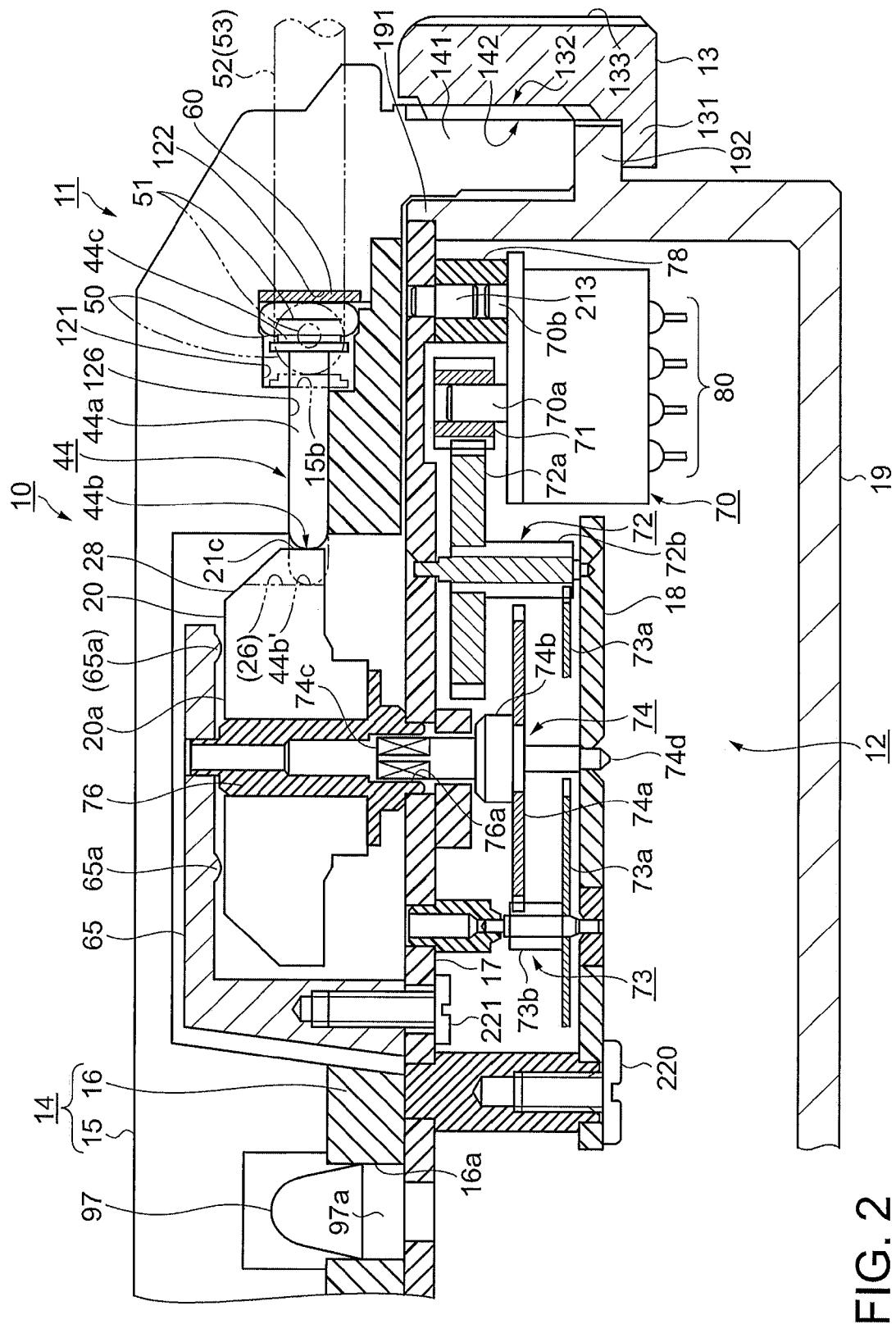
FIG. 2 is a fragmentary sectional view showing a structure of the micropump according to the embodiment 1.

FIG. 2 is a fragmentary sectional view showing a structure of the micropump according to the embodiment. In FIG. 2, in the micropump 10, the tube unit 11 is stacked on a top surface of, and attached to, the control unit 12, and the tube unit 11 and the control unit 12 are connected and integrated by the connecting member 13. Consequently, the tube unit 11 and the control unit 12 are configured in such a way as to be attachable by means of the connecting member 13, and FIG. 2 shows a condition in which they are attached to each other.

Firstly, a description will be given of a configuration and operation of the control unit 12. The control unit 12, including the motor 70 as the drive source, transmits a drive (a rotation) of the motor 70 to a motor transmission wheel 71, a first transmission wheel 72, a second transmission wheel 73, and a cam drive wheel 74. In the embodiment, a wheel train configured of the motor transmission wheel 71, first transmission wheel 72, second transmission wheel 73, and cam drive wheel 74 is the drive force transmission mechanism.

The first transmission wheel 72 is configured of a transmission gear 72a and a pinion 72b, the second transmission wheel 73 is configured of a transmission gear 73a and a pinion 73b, and the cam drive wheel 74 is configured of a transmission gear 74a and a drive shaft 74b. Also, a support shaft 74d is provided at one leading end of the drive shaft 74b, while a cam drive shaft 74c is provided at the other leading end, and the support shaft 74d is inserted in a second casing 18, while the cam drive shaft 74c is inserted in a cam drive wheel fitting hole 76a bored in a tube unit 11 side cam shaft 76. A cross-sectional shape of the cam drive shaft 74c and cam drive shaft fitting hole 76a being, in the embodiment, square, the cam drive shaft 74c is in a freely fitted relationship with the cam drive shaft fitting hole 76a when inserted in it, and their dimensions are set in such a way that a torque of the cam drive wheel 74 is transmittable to the cam shaft 76 in a condition in which the cam drive shaft 74c is fitted in the cam drive shaft fitting hole 76a. Each element of the drive force transmission mechanism is pivotally supported by a first casing 17 and the second casing 18.

Continuing, a description will be given of a structure of connecting the cam shaft 76 and the cam drive wheel 74.

By the cam drive shaft 74c being fitted in, and connected to, the cam drive shaft fitting hole 76a, the drive force from the motor 70 is transmitted from the cam drive wheel 74 to the cam shaft 76, via the drive force transmission mechanism, and a cam 20 presses the tube 50 by means of the plurality of fingers.

A small step motor is employed as the motor 70. The motor 70, although not shown, having a four-pole rotor inside, has two pairs of stators and coils facing the rotor. The motor 70, in a condition in which motor guide shafts 70b implanted upright (in practice, two exist in positions separated from each other) are inserted in a motor holding frame 78, is inserted into motor fixing shafts 213 implanted upright in the first casing 17, and attached to the first casing 17. A plurality of the motor fixing shafts 213 are provided. The motor 70 is connected to a connecting terminal 80. Also, the motor 70 is connected to the unshown control circuitry via the connecting terminal 80.

The control circuitry, being disposed inside the control unit 12, is mounted on a circuit substrate, and divided into blocks, including a control circuit, which carries out a drive control of the motor 70, a memory, and a power control circuit.

Also, the cam 20 is disposed on a top surface (a topmost surface facing the tube unit 11) of the first casing 17. The cam 20, being fixed to the cam shaft 76, rotates with the cam shaft 76 as a rotation center. An upper portion of the cam shaft 76 including the cam 20 is pivotally supported by the cam holding frame 65, while a lower portion thereof is pivotally supported by the first casing 17. The cam holding frame 65 is fixed to the first casing 17 by a fixing screw 221.

Also, the control unit 12 is sealed by a back cover 19. The back cover 19 having a container like form, a fixing portion 191 at an edge thereof is press fitted into an outer periphery of the first casing 17. Consequently, the control unit 12 is configured by the motor 70, drive force transmission mechanism, control circuitry, and cam 20 being integrated into one unit in a condition in which they are held by the first casing 17 and the second casing 18. The drive force (a torque) of the motor 70 being transmitted to the cam 20 via the transmission mechanism, the cam 20 rotates with the cam shaft 76 as the rotation center.

The cam 20 has an outer circumferential surface having concavities and convexities in a range in which the plurality of fingers (as each finger has a common shape, a description will hereafter be given with a finger 44 as an example) press or release the tube 50. Furthermore, a finger guide surface 28 continuous with the outer circumferential surface from a top surface 20a facing the tube unit 11 is provided on the cam 20. The finger guide surface 28, when the tube unit 11 is attached to the control unit 12 from above, guides the tube unit 11 to a position in which cam abutment portions (a cam abutment portion 44b is illustrated) of the plurality of fingers abut against the outer circumferential surface (a finger pressing surface 21c and an arc portion 26 are illustrated). The outer circumferential surface is formed perpendicular to a rotation plane of the cam 20.

It being acceptable that either the finger guide surface 28 is formed as a linear slope, or that it is formed as a convex-topped curved surface, it is more preferable that a connection between the finger guide surface 28 and the outer circumferential surface is smooth finished.

Also, a tilt suppressing protrusion 65a for suppressing the cam 20 tilting in a direction of thickness is formed on the cam holding frame 65. Although the tilt suppressing protrusion 65a is, in the embodiment, formed as a ring whose cross-sectional shape is hemispherical, it also being acceptable to employ point-like protrusions, they are provided in a position near an outer perimeter in a range of the top surface 20a of the cam 20. In the case of employing the point-like protrusions as the tilt suppressing protrusion 65a, they are provided in at least positions facing the plurality of fingers with respect to the cam shaft 76. Also, it is also acceptable to adopt a structure in which the tilt suppressing protrusion is provided on the top surface of the cam 20.

A plan view shape of the cam 20 will be described in detail, referring to FIG. 4.

Next, a description will be given of a structure of the tube unit 11, referring to FIG. 2. The tube unit 11 having a space housing the cam 20 and the cam holding frame 65 in an approximately central portion, the plurality of fingers (the finger 44 is illustrated in FIG. 2) pushed by the outer circumferential surface of the cam 20, and the tube 50 pressed by the plurality of fingers, are held by the guide frame 14 configured of the first guide frame 15 and the second guide frame 16.

The tube 50 is sandwiched between the first guide frame 15 and the second guide frame 16 in a tube guide groove 121 provided in the guide frame 14. In the tube guide groove 121, an elastic member 60 is provided between a tube guide wall 122, against which the tube 50 is pressed by the finger 44, and the tube 50. The elastic member 60 is provided between a range of the tube guide wall 122 in a cross-sectional direction with which the tube 50 makes contact, as well as at least a range thereof in a plan view direction against which the plurality of fingers press the tube 50, in a condition in which the tube 50 is closed, and the tube 50 (also refer to FIG. 4). The elastic member 60 is provided for a purpose of absorbing an excess pressure occurring when the tube 50 is pressed by each finger, improving a tube resistance to a structure in which the tube 50 is pressed directly against the tube guide wall 122. Consequently, it is more preferable to use a low friction coefficient material for an elastic member surface.

The tube 50 and the finger 44, in a condition in which they are respectively mounted inside the tube guide groove 121 and finger guide groove 126 formed in the first guide frame 15 and second guide frame 16, are formed into one unit by welding the first guide frame 15 and the second guide frame 16, or fixing them by means of a fixing screw.

The finger 44 is configured of a shaft 44a, the hemispherical cam abutment portion 44b formed at one end of the shaft 44a, and a tube pressing portion 44c formed of a flange like protrusion formed at the other end. The finger 44 can slide, and move forward and back in an axial direction, in the finger guide groove 126 provided in the first guide frame 15 and second guide frame 16. At this time, the tube pressing portion 44c moves forward and back in the axial direction, between a finger position regulation wall 15b and the tube 50, in the finger guide groove 126, and a movement in a direction of the cam 20 is regulated by the finger position regulation wall 15b. Consequently, the tube pressing portion 44c has a finger 44 stopper function.

The tube pressing portion 44c, on it being released from a pressure of the tube 50 caused by the rotation of the cam 20, moves in a direction toward the cam 20 by means of an elastic force of the tube 50. At this time, the cam abutment portion 44b moves to a position adjacent to the arc portion 26 of the cam 20 (illustrated as a cam abutment portion 44b'). In this way, by providing the flange like tube pressing portion 44c, the finger 44 is prevented from coming off the guide frame 14 when the tube unit 11 stands alone.

Next, a description will be given, referring to FIGS. 2 and 3, of a structure and method of connecting the tube unit 11 and control unit 12. Firstly, as shown in FIG. 2, the tube unit 11 is attached to the control unit 12 from above in the figure. At this time, the tube unit 11 is set by aligning a guide shaft 97 which, acting as a positioning member, is provided on the control unit 12, with a guide hole 16a provided in the second guide frame 16.

The guide shaft 97, being a shaft member whose leading end has a hemispherical shape, is fixed to the first casing 17. Then, a position of the guide shaft 97 is regulated by a guide portion 97a and the guide hole 16a. At this time, the rotation center of the cam 20 matches a center of an arc of the tube guide wall 122.

Next, a description will be given of an engagement between the plurality of fingers and the cam 20.

FIG. 3 is a fragmentary sectional view showing a structure of engagement between the plurality of fingers and the cam 20 in the embodiment. FIG. 3, showing an aspect immediately before the tube unit 11 is attached to the control unit 12, illustrates the finger 44 in the condition shown in FIG. 4. When the tube unit 11 stands alone, the finger 44 itself moves in the direction toward the cam 20 by means of the elastic force of the tube 50 and, as shown in the figure, the cam abutment portion 44b rides on the finger guide surface 28 of the cam 20.

Herein, on the tube unit 11 being pushed down to a control unit 12 side, the cam abutment portion 44b slides following the finger guide surface 28, and the finger 44 moves to a tube 50 side by means of a slope effect of the finger guide surface 28. Then, when the finger 44 reaches the finger pressing surface 21c which is the outer circumferential surface of the cam 20 (the position shown by the two-dot chain line), the tube unit 11 is attached to the control unit 12 in a predetermined position.

At this time, the tube unit 11 and the control unit 12 are attached together in such a way that the rotation center of the cam 20 and the center of the arc of the tube guide wall 122 coincide by means of the guide portion 97a and the guide hole 16a, as shown in FIG. 2.

Herein, when the finger 44 rides on the finger guide surface 28, a pressure acts on the cam 20 such that the cam 20 is tilted in the direction of thickness by the finger 44. However, it is possible to minimize the tilt by means of the tilt suppressing protrusion 65a provided on the cam holding frame 65, causing the slope effect of the finger guide surface 28 to act effectively.

In the kind of operation heretofore described, it is desired to minimize a friction between the cam abutment portion 44b and the finger guide surface 28. Consequently, the cam abutment portion 44b of the finger 44 is smooth finished and, in the embodiment, made hemispherical. In order to reduce the friction, it is possible to select a configuration wherein at least the cam abutment portion is coated with a lower friction coefficient material than that of the cam 20, or the finger itself is formed of a low friction coefficient material.

When the tube unit 11 stands alone before it is attached to the control unit 12, it may happen that the fingers do not press the tube 50, or press the tube due to a variation in dimensions. At this time, a total length of the fingers and an axial position of the tube pressing portions are set in such a way as to obtain a pressing magnitude such that does not cause a tube deterioration due to the fingers continuing to press the tube 50.

Next, a description will be given of a structure of connecting the tube unit 11 and the control unit 12.

As shown in FIG. 2, a flange 141 protruded toward the control unit 12 is provided on an outer periphery of the guide frame 14 (first guide frame 15), and a male thread 142 is formed on an outer periphery of the flange 141. Also, a flange 192 protruded outward is provided on an outer periphery of the back cover 19.

The connecting member 13 is inserted from a back cover 19 side while stacking the tube unit 11 on the control unit 12, and the tube unit 11 and the control unit 12 are connected together by screwing the connecting member 13 on the tube unit 11.

The connecting member 13 being provided with a flange 131 protruded inward and a female thread 132 formed on an inner side of a cylindrical portion, when threadedly connecting the connecting member 13 and the tube unit 11, a circumferential edge of the first guide frame flange 141 is brought into close contact with the flange 192 of the back cover 19, securing a waterproof property of the interior of the micropump 10. The micropump 10 is configured in this way.

In the event of increasing an adhesion by a joint between the circumferential edge of the flange 141 and the flange 192 being provided with a seal member, or coated with a sealant, it is possible to further increase the waterproof property. Also, knurls 133 or irregularities are formed on an outer periphery of the connecting member 13 in order to facilitate a screwing in the cross-sectional direction.

Continuing, a description will be given, referring to the drawings, of a plan view structure of the tube unit 11, and a drive of the micropump, of the embodiment.

FIG. 4 is a plan view showing an outline structure of the tube unit according to the embodiment. FIG. 4 shows a condition in which the micropump 10 is driven in a steady state. Also, it transparently represents the guide frame 14. FIG. 2 is also referred to. In FIG. 4, the tube unit 11 of the embodiment is configured of the tube 50, and seven fingers 40 to 46 interposed between the tube 50 and the cam 20, radiating from a rotation center P (which matches the rotation center of the cam 20) of the cam shaft 76. The fingers 40 to 46 are each radially disposed at even intervals.

The cam 20 being fixed to the cam shaft 76, finger pressing surfaces 21a to 21d are formed on the outer circumferential surface having the concavities and convexities in a circumferential direction. The finger pressing surfaces 21a to 21d are formed on a concentric circle equally distant from the rotation center P. Circumferential pitches and outer shapes of the finger pressing surfaces 21a and 21b, finger pressing surfaces 21b and 21c, finger pressing surfaces 21c and 21d, and finger pressing surfaces 21d and 21a are formed so as to be equal. Pitches between adjacent finger pressing surfaces are equal.

Each of the finger pressing surfaces 21a to 21d is formed so as to be continuous with a finger pressing slope 22 from an arc portion 23 on the concentric circle having the rotation center P as its center. The arc portions 23 are provided in a position in which they do not press the fingers 40 to 46.

Also, one end of each of the finger pressing surfaces 21a, 21b, 21c and 21d, and each of the arc portions 23, are connected by a linear portion 24 extended from the rotation center P.

Also, the tube 50, which causes the liquid to flow, is disposed in a position separated from the cam 20. The tube 50, having elasticity, in the embodiment, is formed of silicon rubber. The tube 50 is mounted in the tube guide groove 121 formed by the first guide frame 15 and second guide frame 16 (refer to FIG. 2), and one end, being the flow outlet portion 53 which discharges the liquid to an exterior, protrudes outwardly from the micropump 10. The other end, being the flow inlet portion 52 which causes the liquid to flow in, is connected to the unshown reservoir containing the liquid.

The tube 50 is mounted in the tube guide groove 121 formed in such a way that a range thereof which is pressed by the fingers 40 to 46 forms a concentric circle having the rotation center P as its center. The fingers 40 to 46, as they are formed in the same shape, will be described with the finger 44 as an example. The finger 44 is configured of the column like shaft 44a, the tube pressing portion 44c provided at the one end of the shaft 44a, and the cam abutment portion 44b with the other end rounded hemispherically.

The fingers 40 to 46, being able to move forward and back along the finger guide grooves 126, by being pressed in an outward direction from the rotation center P by the cam 20, press the tube 50, and close a liquid flow portion 51. A central position of the fingers 40 to 46 in a cross-sectional direction approximately coincides with a center of the tube 50.

Continuing, a description will be given, referring to FIG. 4, of an operation relating to a liquid conveyance according to the embodiment. The cam 20 is rotated (in a direction of the arrow R shown in the figure) via the drive transmission mechanism by the motor 70. The finger 44 is pressed by the finger pressing surface 21d of the cam 20, and the finger 45 abuts against a connection between the finger pressing surface 21d and the finger pressing slope 22, closing the tube 50. Also, the finger 46 presses the tube 50 on the finger pressing slope 22, but the finger 46, a pressing magnitude of which is smaller than that of the finger 44, does not completely close the tube 50.

The fingers 41 to 43, being in a range of the arc portion 26 of the cam 20, are in an initial position in which they do not press. Also, the finger 40 abuts against the finger pressing slope 22 of the cam 20, but has not yet closed the tube 50 in this position.

On the cam 20 being further rotated in the direction of the arrow R from this position, the fingers 45 and 46 are pressed in this order by the finger pressing surface 21d of the cam 20, closing the tube 50. The finger 44 is freed from the finger pressing surface 21d, releasing the tube 50. The liquid flows into the liquid flow portion 51 in a position of the tube 50 in which the tube 50 is released from the closing by the finger, or in a position in which it has not yet been closed.

On the cam 20 being further rotated, the finger pressing slope 22 sequentially presses the fingers 40, 41, 42 and 43 in this order, and each of the fingers 40, 41, 42 and 43, when it reaches the finger pressing surface 21c, closes the tube 50.

By this kind of operation being repeated, the liquid is caused to flow in a direction from a flow inlet portion 52 side to a flow outlet portion 53 side, and discharged from the flow outlet portion 53.

At this time, two of the plurality of fingers abut against a finger pressing surface of the cam 20 and, when the finger pressing surface moves to a position in which to press a next finger, it presses one of the fingers. By the condition in which two fingers are pressed, and the condition in which one finger is pressed, being repeated in this way, a condition is created in which at least one finger always closes the tube 50. A micropump structure using this kind of motion is called a peristaltic drive system.

Consequently, according to the heretofore described embodiment 1, as the tube 50 and the fingers 40 to 46 are formed into one unit by the guide frame 14, it being possible to replace the tube 50 as the tube unit 11, it is possible for a user to easily carry out a tube replacement. Moreover, as it is possible to adjust the tube pressing magnitude by adjusting the finger length for each tube unit with respect to a variation in diameter of the tube 50, there is an advantage of easily ensuring a discharge accuracy.

Also, as the tube pressing magnitude is stabilized, as heretofore described, it being possible to make a maximum load torque of the motor 70 largely constant, as well as it being possible to eliminate an overload on the motor 70, and obtain a desired drive performance, it is possible to prevent a kind of drive failure due to the overload, enabling a realization of a highly reliable micropump.

Also, as the control unit 12 includes the motor 70, it not being necessary to bring the motor 70 and the drive force transmission mechanism out of engagement, it is possible to make a drive system formed of the motor 70 and the drive force transmission mechanism a configuration having a stable engagement condition.

Furthermore, in a case in which a liquid to be used is a liquid medicine or the like, in the event that the tube unit 11 and the reservoir in which is contained the liquid medicine are formed into one unit, and the tube unit 11 including the tube 50 which makes direct contact with the liquid medicine is prepared for each targeted liquid medicine, it is possible to prevent a use of an erroneous kind of liquid medicine, or a mixing of different kinds of liquid medicine.

Also, as the control unit 12 includes the motor 70, the tube unit 11 is a unit formed of the tube 50, fingers 40 to 46, and guide frame 14, and the control unit 12 is a unit formed of the cam 20, drive force transmission mechanism, motor 70, and control circuitry. Consequently, as the tube unit 11 has a smaller number of components, and is lower in cost, than the control unit 12, in the event that the control unit 12 is made reusable, and the tube unit 11 is made disposable, it is possible to reduce a running cost.

Also, the cam 20 has the finger guide surface 28 for guiding the cam abutment portion of each of the plurality of fingers to the position in which it abuts against the outer circumferential surface of the cam 20 when the tube unit 11 is attached to the control unit 12. For this reason, the cam abutment portion of each finger slides along the finger guide surface 28, and moves to a space between the cam 20 and the tube 50. Consequently, it is possible to house the tube 50 in a position in which the tube 50 can be pressed by the cam 20, without carrying out a special operation.

Also, it is possible to prevent the cam 20 or the fingers 40 to 46 from being destroyed when the tube unit 11 is attached to the control unit 12.

In the micropump 10, as the plurality of fingers are moved in a direction in which to press the tube by the cam 20 rotating, they are each disposed radiating from the rotation center P of the cam 20. Consequently, as the center of the arc of the tube guide wall 122 and the rotation center P of the cam 20 coincide by providing the guide shaft 97 as the positioning member, it being possible to make an amount of movement of each of the plurality of fingers constant, it is possible to suppress a variation in the amount of movement of each finger (that is, the tube pressing magnitude).

Also, as heretofore described, when the tube unit 11 is attached to the control unit 12, the cam abutment portions of the fingers 40 to 46 slide along the finger guide surface 28, and the fingers 40 to 46 move to the space between the cam 20 and the tube 50. Also, when driving the micropump 10, the outer circumferential surface of the cam 20 slidingly presses the cam abutment portions. Consequently, a friction load occurring due to the sliding being reduced by finishing the cam abutment portions so as to be hemispherical and smooth, or forming the fingers of a low friction coefficient material, it is possible to reduce a load on the motor 70, and improve a drive stability and endurance.

Also, as the elastic member 60 is provided between the tube guide wall 122 and the tube 50, by an excess pressure being absorbed by the elastic member 60 when the tube 50 is pressed by the fingers 40 to 46, it is possible to improve the resistance of the tube 50 to the structure in which the tube 50 is pressed directly against the tube guide wall 122.

It is more effective to use a low friction coefficient material as the elastic member 60.

Also, by providing the cam 20 with the tilt suppressing protrusion 65a which suppresses the tilt of the cam 20 in the direction of thickness, it is possible, in the event that the cam abutment portions ride on the finger guide surface 28 when the tube unit 11 is attached to the control unit 12, to prevent the cam being tilted to impede a movement of the fingers to an appropriate finger position.

Furthermore, it is also possible, when driving the micropump, to prevent a condition in which the fingers press the tube varyingly due to a wobbly rotation of the cam 20 in the direction of thickness.

Also, by regulating a position of the fingers 40 to 46 in a forward-back direction by means of the flange like tube pressing portions provided on the fingers 40 to 46, and the tube guide grooves 121 provided in the tube frame 14, it is possible to prevent the fingers 40 to 46 from coming off the guide frame 14 when the tube unit stands alone.

Furthermore, the position of the fingers 40 to 46 in the forward-back direction is also regulated when the tube unit 11 is attached to the control unit 12. Consequently, it is possible to cause the cam abutment portions of the fingers 40 to 46 to slide on the finger guide surface 28, and reliably move the fingers 40 to 46 to a predetermined position. By this means, it is possible to prevent the cam 20 or the fingers 40 to 46 from being destroyed.

Also, as the fingers 40 to 46 are held on the guide frame 14 in the position in which they do not press the tube 50, or in the condition in which they press the tube 50 to the extent that the tube 50 does not deteriorate, it is possible to prevent a deterioration of the tube 50 which is conceivable in the event that the tube 50 is maintained in a pressed condition over a long period.

Another Example of Embodiment 1

As a structure of regulating the position of the fingers 40 to 46 in the forward-back direction, it is possible to employ a structure in which a flange like protrusion acting as a stopper is provided partway along the shaft of each finger.

FIG. 5 is a fragmentary sectional view showing a micropump according to another example of the embodiment 1. A description will be given with the finger 44 as an example. In FIG. 5, the finger 44 has a stopper 44e, as the flange like protrusion, formed partway along a shaft 44a in an axial direction. The one end of the shaft 44a, being the cam abutment portion 44b, has the same shape as in the heretofore described embodiment 1 (refer to FIGS. 2 and 4), while the other end is the tube pressing portion 44d.

Also, a stopper groove 30 is formed in the guide frame 14 (first guide frame 15 and second guide frame 16), and the stopper 44e of the finger 44 is housed therein. A forward and back position of the finger 44 is regulated by the stopper 44e and the stopper groove 30 while the finger 44 is being held between the first guide frame 15 and the second guide frame 16.

Then, on a cam 20 side, the position in which the cam abutment portion 44b rides on the finger guide surface 28 of the cam 20 is regulated to a position in which the stopper 44e abuts against a stopper wall 30b of the stopper groove 30. Also, on the tube 50 side, a position of a stopper wall 30a is set in such a way as to be deep enough for the cam 20 to push the tube pressing portion 44d to the position in which to close the tube 50.

Even by adopting this kind of configuration, in the same way as in the embodiment 1, it being possible to prevent the fingers 40 to 46 from coming off the guide frame 14 when the tube unit 11 stands alone, it is possible to cause the cam abutment portions of the fingers 40 to 46 to slide on the finger guide surface 28, and reliably move the fingers 40 to 46 to the predetermined position.

Embodiment 2

Continuing, a description will be given of the micropump according to an embodiment 2, referring to the drawings. The embodiment 2 has a feature wherein a motor which drives a cam is provided in a tube unit. Consequently, an illustration and description will be given centered on differing points. The same functional components and regions as those of the embodiment 1 are indicated by the same reference numbers and characters.

FIG. 6 is a fragmentary sectional view showing the micropump according to the embodiment 2. FIG. 6 shows a condition in which the tube unit 11 and the control unit 12 are connected, and ready to be driven. In FIG. 6, the motor 70 is attached to the tube unit 11. Consequently, the tube 50 and the plurality of fingers, and the motor 70 are formed into the tube unit 11 while being held by the guide frame 14. On the other hand, the control unit 12 is configured of the cam 20, the drive force transmission mechanism, and the control circuitry.

The motor 70 is fixed by press fitting the motor guide shafts 70b (the plurality of them are provided) into the second guide frame 16, and accurately regulating an accurate relative position between the motor transmission wheel 71 and a motor drive shaft 70a in the plan view direction. The motor drive shaft 70a, being formed in such a way that a cross-sectional shape is square, is inserted and fitted into a motor shaft fitting hole 71c, bored in the motor transmission wheel 71, a cross-sectional shape of which is square.

The motor transmission wheel 71 is configured of a gear 71a and a support shaft 71b, and a leading end 71d is urged in an axial direction of the motor drive shaft 70a by a motor transmission wheel spring 210 acting as an elastic member. In this condition, the gear 71a of the motor transmission wheel 71 and the transmission gear 72a of the first transmission wheel 72 are connected in mesh. Consequently, the drive force of the motor 70 is transmitted to the tube unit 11 via the first transmission wheel 72.

The motor 70 is connected to a motor substrate 230 by the connecting terminal 80. The motor substrate 230, as it is disposed in the tube unit 11, is connected to the control circuitry disposed on the control unit 12 side using a contact pin or the like (not shown).

When the motor drive shaft 70a and the motor shaft fitting hole 71c are out of phase with each other in a direction of rotation when the tube unit 11 is attached to the control unit 12, four corner ends of the motor drive shaft 70a are abutted against a circumferential edge of the motor shaft fitting hole 71c, pushing the motor transmission wheel 71 down to a second casing 18 side. Then, the motor transmission wheel 71 flexes the motor transmission wheel spring 210 by means of the leading end 71d. The gear 71a of the motor transmission wheel 71 does not come out of mesh with the transmission gear 72a of the first transmission wheel 72. Consequently, even in the event that the tube unit 11 and the control unit 12 are connected in this kind of condition, it does not happen that the motor drive shaft 70a and the motor transmission wheel 71 are destroyed.

Then, on the motor 70 being driven from the heretofore described condition, the motor drive shaft 70a and the motor shaft fitting hole 71c come into phase with each other in the direction of rotation, the motor transmission wheel 71 is moved in a direction of the motor 70 by the motor transmission wheel spring 210, and the motor drive shaft 70a is fitted in, and connected to, the motor shaft fitting hole 71c. At this time, the gear 71a of the motor transmission wheel 71 moves in a condition in which it meshes with the transmission gear 72a of the first transmission wheel 72, and takes on the kind of condition shown in FIG. 6 in which the drive force can be transmitted.

In a case in which the micropump 10 is mounted on or inside a living body, as a micromotor is also used as its motor, and a size of components of the motor 70 is very small, it can be predicted that it is impossible to secure the endurance, due to an overload caused when driving the tube unit 11 (cam 20). At this time, it is possible to make a replacement, including the motor 70, at a timing of a replacement of the tube unit 11 (that is, a replacement of the tube 50). Consequently, it being possible to always stably maintain the drive performance of the motor 70, it is possible, in the event of miniaturizing the motor, to use it without worry.

Also, as it is possible to make a replacement as a unit, including the motor 70, when replacing the tube unit 11, it not being necessary to remove the motor 70 from the tube unit 11 (in the embodiment 1, the control unit 12), there is also an advantage that an operability is improved.

Furthermore, as the control unit 12 is not provided with the motor 70, which is inferior in endurance to the drive force transmission mechanism and the control circuitry, it is possible to continue to use the control unit 12 over a longer period.

The invention not being limited to the heretofore described embodiments, a modification, an improvement and the like not departing from the scope of the invention are included in the invention.

Also, the micropumps 10 according to the heretofore described embodiment 1 and embodiment 2, being able to be miniaturized, can cause a minute flow volume to flow stably and continuously. Consequently, the micropumps 10, being mounted inside the living body, are suitable for a medication such as a development of a new medicine but, by being mounted inside or outside various mechanical apparatus, can be used for a conveyance of a fluid such as water, salt water, a liquid medicine, oil, an aromatic solution, ink, or a gas. Also, it is possible to use the micropumps alone for a flow and supply of the fluid.

What is claimed is:

1. A micropump comprising:
    a tube unit including a tube which has elasticity, and one portion of which is disposed in an arc shape, a plurality of fingers, which are disposed radiating from a direction of a center of the arc shape of the tube, and a guide frame, which holds the tube and the plurality of fingers; and
    a control unit including a cam, which sequentially presses the plurality of fingers in a direction in which a liquid flows, a drive force transmission mechanism, which transmits a torque to the cam, and a control circuitry, which carries out a control of a motor which drives the drive force transmission mechanism,
    wherein the tube unit and the control unit are attached stacked one on the other, and are detachable,
    the cam includes an outer circumferential surface, which is approximately perpendicular to a rotation plane of the cam, and has concavities and convexities which cause the plurality of fingers to press or release the tube, and a slope or a curved surface, which is continuous with the outer circumferential surface from a surface facing the tube unit, and
    when the tube unit is attached to the control unit, cam abutment portions of the plurality of fingers are moved to a position, in which they abut against the outer circumferential surface, along the slope or curved surface.

2. The micropump according to claim 1, wherein a positioning member is provided for approximately aligning a rotation center of the cam with a center of an arc of a tube guide wall in a range in which the plurality of fingers press the tube, when the tube unit is attached to the control unit.

3. The micropump according to claim 1, wherein the cam abutment portions of the plurality of fingers are formed as a smooth curved surface, or formed of a low friction coefficient material.

4. The micropump according to claim 1, wherein an elastic member is provided between the tube guide wall, provided in the guide frame and subject to a pressure of the plurality of fingers, and the tube.

5. The micropump according to claim 1, wherein the control unit further including a cam holding member which pivotally supports the cam, a tilt suppressing protrusion which suppresses a tilt of the cam in a direction of thickness is provided on the cam or the cam holding member.

6. A tube unit which is attachable to and detachable from the control unit according to claim 1, comprising:
    a tube, which has elasticity, a plurality of fingers, which sequentially press the tube in a direction in which a liquid flows, and a guide frame, which holds them.

7. The tube unit according to claim 6, which is attachable to and detachable from the control unit, comprising:
    the tube, the plurality of fingers, a motor, which drives a drive force transmission mechanism which transmits a torque to a cam which sequentially presses the plurality of fingers in the direction in which the liquid flows, and a guide frame, which holds them.

8. The tube unit according to claim 6, wherein
    each of the plurality of fingers includes a shaft, a cam abutment portion provided at one end of the shaft, and a tube pressing portion which, being provided at the other end, is configured of a flange like protrusion, and
    a groove, which houses the tube pressing portion and has a finger position regulation wall which regulates a position of each of the plurality of fingers in a forward-back direction, is provided in the guide frame.

9. The tube unit according to claim 6, wherein
    each of the plurality of fingers includes a shaft, a cam abutment portion provided at one end of the shaft, and a tube pressing portion provided at the other end,
    a flange like protrusion is provided partway along the shaft, and
    a groove, which houses the flange like protrusion and regulates a position of each of the plurality of fingers in a forward-back direction, is provided in the guide frame.

10. The tube unit according to claim 6, wherein
    the plurality of fingers are held on the guide frame in a position in which they do not press the tube, or in a condition in which they press the tube to the extent that the tube does not deteriorate.

11. A control unit which is attachable to and detachable from the tube unit according to claim 1, comprising:
    a cam, which sequentially presses a plurality of fingers in a direction in which a liquid flows, a drive force transmission mechanism, which transmits a torque to the cam, and a control circuitry, which carries out a drive control of a motor which drives the drive force transmission mechanism.

12. The control unit according to claim 11, comprising:
    the cam, the drive force transmission mechanism, the control circuitry, and the motor.

* * * * *